United States Patent
Hernan Izquierdo et al.

(10) Patent No.: US 9,642,354 B2
(45) Date of Patent: May 9, 2017

(54) METHOD OF FREEZING CELLS

(75) Inventors: Roberto Hernan Izquierdo, Cantabria (ES); Natalia Gallot Escobal, Vizcaya (ES); Antonio Cruz Pacheco, Cantabria (ES)

(73) Assignee: Cellulis, S.L., Santona Cantabria (ES)

( * ) Notice: Subject to any disclaimer, the term of this patent is extended or adjusted under 35 U.S.C. 154(b) by 467 days.

(21) Appl. No.: 13/997,408

(22) PCT Filed: Dec. 15, 2011

(86) PCT No.: PCT/EP2011/006579
§ 371 (c)(1),
(2), (4) Date: Jul. 29, 2013

(87) PCT Pub. No.: WO2012/089337
PCT Pub. Date: Jul. 5, 2012

(65) Prior Publication Data
US 2014/0004500 A1    Jan. 2, 2014

(30) Foreign Application Priority Data
Dec. 30, 2010   (EP) .................... 10016179

(51) Int. Cl.
*A01N 1/02*    (2006.01)

(52) U.S. Cl.
CPC ......... *A01N 1/0284* (2013.01); *A01N 1/0221* (2013.01); *A01N 1/0268* (2013.01)

(58) Field of Classification Search
None
See application file for complete search history.

(56) References Cited

U.S. PATENT DOCUMENTS

2008/0092560 A1* 4/2008 Loa ...................... A01N 1/0289 62/60
2010/0297600 A1* 11/2010 Cecchi ................. C12M 21/06 435/1.3

FOREIGN PATENT DOCUMENTS

| EP | 1869976 A1 | 12/2007 |
| WO | WO 2005052138 | * 6/2005 |
| WO | WO2007059084 A2 | 5/2007 |

OTHER PUBLICATIONS

Chang et al., Changes in membrane structure induced by electroporation as revealed by rapid-freezing electron microscopy, Biophys. J., vol. 58, Jul. 1-12, 1990.*
Falkow et al., The Prokaryotes: vol. 4: Bacteria: Firmicutes, Cyanobacteria (2006).*
Armitage WJ, Juss BK, "Freezing Monolayers of Cells Without Gap Junctions", Cryobiology, Apr. 2003; 46(2):194-6, Bristol, U.K.
Liu B, McGrath JJ, "Effects of Two-Step Freezing on the Ultra-Structural Components of Murine Osteoblast Cultures", Cryo Letters, Nov.-Dec. 2006; 27(6):369-74; Shanghai, China.
Acker JP, Elliot JA, McGan LE, "Intercellular Ice Propagation:Experimental Evidence for Ice Growth Through Membrane Pores", Biophys J. Sep. 2001;81(3):1389-97, Edmonton, Canada.

* cited by examiner

*Primary Examiner* — Suzanne M Noakes
*Assistant Examiner* — Stephen Chong
(74) *Attorney, Agent, or Firm* — Timothy J. Monahan; Monahan & Company, LLC (57) ABSTRACT

The invention discloses a multi-layer cell freezing vial and method of obtention thereof. The method of obtention is a cell freezing and thawing process that avoids the need of incorporating new fresh medium to the thawed cells for the dilution of the cryoprotective agent. This is achieved by the previous freezing of an extra layer of culture medium in addition to the frozen cell solution containing said cryoprotective agent. At the time of thawing, the culture medium and the cell solution mix themselves, turning the concentration of said cryoprotective agent to a non-toxic dilution and achieving the effective exclusion of said cryoprotective agent from the living cells.

20 Claims, 5 Drawing Sheets

METHOD OF FREEZING CELLS

CROSS REFERENCE TO RELATED APPLICATION

This Application is a 371 of PCT/EP2011/006579 filed on Dec. 15, 2011, which claimed the priority of EP Patent Application No. 2010-10016179.3 filed on Dec. 30, 2010, both applications are incorporated herein by reference in their entirety.

FIELD OF THE INVENTION

The invention discloses a multi-layer cell freezing vial and method of obtention thereof. The viability and durability of the frozen cells is increased after the method of the Invention. It is useful in cell-based assays for basic research, diagnostics and drug development applications in the biotechnology and pharmaceutical sector.

BACKGROUND ART

In vitro cultured cells, including mammalian cells, are extensively used in cell biology studies. Until the middle 80's, cell culture techniques were labor-intensive and did not scale to high cell numbers. Currently, there is a wide acceptance and universal application of High Throughput Screening (HTS) using cell-based assays in the Pharmaceutical and Biotechnology industry as well as in basic research.

HTS screening is performed in microplates. The surface of these microplates may be modified for cell culturing applications, typically using a plasma discharge for easier cell attachment. These cell culture microplates have eased larger scale cultivation of cells impacting both drug discovery and manufacturing. With respect to drug discovery, cell-based assays are increasingly being used for drug target validation in efficacy studies using high content analyses, and also in vitro ADMET (drug absorption, distribution, metabolism, elimination and toxicity). These studies are performed on cells as they provide more representative responses to drugs than simple molecular assays, and are easier to use in a high-throughput format than animals.

Cryopreservation is the gold standard method for long term storage of cultured cells. Since cryopreservation can adversely affect the viability and function of cells, methodological freezing and thawing procedures have been developed in order to preserve the correct structure, function, behaviour and biology of cells in culture. In early years, the addition of cryoprotective agents including glycerol and dimethyl sulphoxide (DMSO) were already used both for the preservation of tumour cells and also for healthy hematopoietic primary cells. In general, current standards indicate that long term frozen cells are stored at −130° C. or below in liquid nitrogen vapour phase to ensure the highest level of viability. For shorter periods of time commonly used for transportation purposes (usually from 1 to 3 days), frozen cells can be stored between −70° C. and −80° C.

Frozen cells may be contained in straws or, more commonly, in ampoules of 1 ml to 5 ml also known as cryovials or cryotubes, with a 10% of cryopreservant.

Basic thawing conditions are already established in the art as beneficial for the recovery of the cells. These thawing conditions remain as current standard protocols and include thawing temperature optimization, dilution of cryopreserved solution by adding cell culture medium with serum or complete cryoprotective agent removal by centrifugation. These standard thawing protocols (e.g. ATCC protocols) indicate that the cryovial has to be thawed rapidly by placing it in a water bath at 37° C. and continuous agitation is applied until its contents have been thawed completely. Then, the vial is decontaminated and the content is immediately transferred to a culture vessel containing normally up to 10 volumes of appropriate culture medium. This dilution is performed drop-wise in order to minimize as possible the osmotic shock. It will lower the cryoprotective agent's concentration (commonly DMSO) to a level that does not need its immediate complete removal for most cells. The entire thawing operation must be done as fast as possible in order to minimize the toxic effects of the cryoprotective agent to the cells. Upon cell attachment, commonly within the next 24 hours of incubation at 37° C. in a 5% $CO_2$ atmosphere, the medium is replaced with a fresh one and that expedites the removal of the cryoprotective agent. For cell types more sensitive to the cryoprotective agent, centrifugation must be performed before seeding in order to completely remove the toxic agent.

Cell cultures are typically expanded in vitro and harvested at a confluence of 80% or more. Several methods are used in the art for harvesting cell cultures, including enzymatic digestion using trypsin and EDTA, mechanical lifting using cell scrapers, or temperature responsive surfaces i.e. UpCell™ from Nunc. After cell harvesting, cells are commonly centrifuged, diluted, counted using a haemocytometer or an automatic cell counter and either seeded again or suspended at the right concentration of cryoprotective agent.

Cells are seeded in regular cell culture vessels also called flasks, grown in vitro for few days and then re-seeded into microplates when high-throughput use is required. This tissue culture process is still the current standard for seeding cells in a high throughput format, being a laborious and time consuming method that requires proper cell culture facilities and qualified technicians. The result is exposed to microbial contamination and cross-contamination of the cells due to the numerous handling procedures involved.

JR 2002253205 A has tried to address this issue by directly freezing down cells that are adhered to a plate. US 2002012901 A1 teaches about thawing methods also related to adherent frozen cells. However, it is well known that cells frozen in monolayers are more susceptible to freezing injury than those in suspension. It has been reported that it might be due to the presence of gap junctions that ease the spread of ice between neighboring cells (Armitage et al. Cryobiology 2003; Liu et al. Cryo letters 2003, Acker J P et al., 2001). JR 2069200 A and CA 2689946 A1 teach about adherent frozen cells on plates and just focused on diagnostic tests to reveal intracellular parasites and viruses. None of these methods teach about several-layer frozen vials as per in the present invention.

WO 2006072335 A1 and EP 1869976 are considered the closest prior art publications, teaching about suspended cells frozen in muitiwell plates at an oxygen partial pressure lower than atmospheric pressure at the time of cell freezing in order to extend their shelf life. None of these two publications teach about higher-efficiency several-layer frozen vials, and these methods need indeed to dilute by the addition of culture medium to the thawed cells before performing any cell-based assay, in order to avoid the toxic effect of the cryoprotective agent, unlike the present invention. However, searching for a similar shelf-life effect, a preferred embodiment of the invention describes a last layer of hypoxic medium.

The problem of the art is then to provide a freezing method that could result in better post-thawing cell viability, in the save of time at tests performance and in diminish contamination risks. The solution provided by the present invention is a sequential freezing method resulting in a double or triple layered body container, which includes at least one fresh diluent layer. This method ease the thawing process in one single step, increases the thawing efficiency in a minimum of 15% and avoids the exchange of the viable cells to another container, thus diminishing contamination risks.

DESCRIPTION OF THE INVENTION

The invention is a cell freezing and thawing method that avoids the need of incorporating new fresh medium to the thawed cells for the dilution of the cryoprotective agent. This is achieved by the previous freezing of an extra layer of medium or diluent in addition to the frozen cell solution containing said cryoprotective agent. At the time of thawing, the diluent and the cell solution mix themselves taking the concentration of the cryoprotective agent to a non-pathogenic dilution, achieving the effective separation of said cryoprotective agent from the living cells whether letting it flow to the bottom or to the surface of the resulting solution pending on the molecular weight of said agent, and minimizing the osmotic shock of the cells with the solutes due to their progressive mixing. This is the common inventive concept of the present invention.

At least two possibilities are comprised within this inventive concept: 1) the frozen cell solution to lay onto the frozen diluent. The layer of living cells comprising the cold cryoprotective agent will be immediately frozen at a temperature ratio of 1° C. per minute or faster. In this case, the cryoprotective agent should be of higher molecular weight than the diluent; for example, DMSO or glycerol. And 2) the frozen cell solution to lay beneath the frozen diluent, with the chosen cryoprotective agent of lower molecular weight than the diluent; for example methanol. When thawed, the cryoprotective agent will flow upwards the mixture separating itself from the living cells, which will survive in a great percentage. The inventive concept remains the same: when thawed, the mixture of fresh diluent and cell solution dilutes the cryoprotective agent. This enables to avoid the cell expansion phase that follows cell thawing after the general proceedings of the art, leading the invention to a considerable save of time at any assay performance.

A first embodiment of the invention is then a method of freezing cells or cell-like materials or non-human embryos, said method comprising the steps of: freezing a layer of biologically acceptable liquid diluent in a container; adding onto said frozen diluent a layer of said cells or cell-like materials or non-human embryos in form of a solution, the medium of said solution comprising at least one cryoprotective agent in suitable concentration; and freezing the result of the previous step to obtain a double-layer frozen body with the frozen cells or cell-like materials or non-human embryos solution on top; or: freezing a layer of cells or cell-like materials or non-human embryos in form of a solution, the medium of said solution comprising at least one cryoprotective agent in suitable concentration, in a container; adding onto said frozen solution a layer of biologically acceptable liquid diluent; and freezing the result of the previous step to obtain a double-layer frozen body with the frozen diluent on top.

In the scope of the present application, the expression "to freeze" means to decrease the temperature of the liquid diluent or cell solution below their respective glass transition temperature to form a frozen body.

In the scope of the present invention, the term "cell like materials"" refers to cell organelles, cell membranes or liposomes.

In the scope of the present invention, the term "biologically acceptable liquid diluent" refers to any liquid diluent compatible with cells living in healthy in vitro conditions.

Another embodiment of the invention is to repeat any these freezing series to obtain a multi-layer frozen body. The multi-bodied container is also a preferred embodiment of the invention as far as said container includes the disclosed layer sequence.

The layered structure of the invention is capable of lowering the toxic effect of the cryoprotective agent and decreasing the osmotic shock to the cells during the thawing process. Clue is that the layer containing the said cells must be not greater than half the volume of the diluent layer, to ensure a proper dilution. Thus, a particular embodiment of the method of freezing cells or cell-like materials or non-human embryos of the invention is that the volume of said cells or cell-like materials or non-human embryos solution layer is equal or less than the diluent layer, more preferably equal or less than half the volume of said liquid diluent layer.

Another preferred embodiment is the method of freezing cells or cell-like materials or non-human embryos of the invention, comprising the additional steps of adding, onto the frozen cells or cell-like materials or non-human embryos solution on top of the double-layer frozen body, a layer of hypoxic biologically acceptable liquid diluent, and freezing the result to obtain a triple-layer frozen body. Preferably, said hypoxic biologically acceptable liquid diluent is an anoxic biologically acceptable liquid diluent. This extra hypoxic layer must also be evenly dispensed at a temperature close to 0° C. in the top of the cell solution frozen layer and quick frozen at a temperature of −70° C. or less. The amount of liquid must be enough to seal completely the container so that the frozen cells are confined and surrounded by the diluent. An improved shelf life of the frozen cells is achieved by the addition of this hypoxic layer, in a similar manner of the effect taught by the art of using a hypoxic atmosphere at the time of freezing. The triple-layer method embodiment increases the preservation time of the container at −80° C. up to 6 months.

In the scope of the present invention, the term "hypoxic" refers to a condition by which the partial pressure of the oxygen in the diluent is below the optimal level for the cell metabolism, typically between 120 and 150 mm Hg. A valid example for a hypoxic solution within the scope of the invention is a oxygen partial pressure of 20 mm Hg or less.

In the scope of the present invention, the term "anoxic" means a condition by which the partial pressure of the oxygen in the diluent is equivalent to zero.

In a very preferred embodiment of the method of the invention said biologically acceptable liquid diluent is complete cell culture medium, even more preferably supplemented with at least one antibiotic and/or serum. In another preferred embodiment of the invention said cryogenic agent is selected among the group of DMSO, glycerol, polyvinylpyrrolidone, ethylene glycol, methanol, methyl acetamide and sugars; more preferably DMSO.

In another embodiment of the invention, the freezing cells are microorganisms, and in another one, the freezing cells are plant cells. In a preferred embodiment, the freezing cells are animal cells, more preferably animal cells selected from the group of tumour cell lines, immortalized cell lines, continuous cell lines, genetically modified cell lines, division arrested cells, stem cells, induced pluripotent stem cells and primary isolated cells. Even more preferably, said primary isolated cells are selected from the group of epithelial cells, endothelial cells, mesenchymal cells, hematopoietic cells. In a preferred embodiment of the invention said animal cells are mammal cells, more preferably oocytes or sperm.

In the scope of the present invention, the term "tumour cell lines" refers to permanently established cell culture lines originated from in vivo tumours.

In the scope of the present invention, the term "immortalized cell lines" refers to those lines of cells genetically engineered to reproduce themselves indefinitely.

In the scope of the present invention, the term "continuous cell lines" refers to those lines of cells that are able to reproduce in vitro indefinitely.

In the scope of the present invention, the term "genetically modified cell lines" refers to those cells lines whose genetic material has been modified or altered, typically through genetic engineering techniques.

In the scope of the present invention, the term "division arrested cells" refers to those cells whose cell cycle has been artificially arrested; that is, to which their division ability has been turned inoperable. These are mainly used for high throughput screening purposes.

In the scope of the present invention, the term "stem cells" refers to those cells that own the ability to go through numerous cell division cycles while maintaining the undifferentiated state, and at the same time are pluripotent able to differentiate into specialized cell types, with the exception of human embryo stem cells.

In the scope of the present invention, the term "induced pluripotent stem cells" refers to those cells that derive from adult somatic non-pluripotent cells, and have been genetically reprogrammed to loose their tissue-specific qualities and become pluripotent.

In the scope of the present invention, the term "primary isolated cells" refers to those cells that are directly obtained from the tissue of a subject.

In another embodiment of the invention, the method of freezing cells or cell-like materials or non-human embryos is performed in a multi-well plate, a vial, a straw, a vessel, a flask or a dish.

Another preferred embodiment is any of the double-layer frozen bodies of the invention, and the container comprising said double-layer frozen body. And still another embodiment is the triple-layer frozen body of the invention and the container containing same. A very preferred embodiment of the invention is that said container is a well of a 96-well microplate, a well of a 384-well microplate or a well of a 1536-well microplate. One of the most preferred embodiments is a HTS format ready-to-use multi-wed plate comprising at least one of the double-layer and/or triple-layer frozen bodies of the invention.

When the container of the invention is thawed in a warm temperature atmosphere, typically $CO_2$ incubator at 37° C., the frozen layers melt in a progressive manner so that the osmotic shock is minimized and the cells get uniformly mixed with the diluent. This "self-seeding" method avoids further cell handling, and allows adherent cells to drop and attach to the bottom of the container or well in case of a microplate, by gravity. At the same time, the diluted cryoprotective agent turns the environment appropriate for the fast recovery of the cells. Typically, within the next 2 hours of incubation, the medium of each well may be replaced with fresh complete cell culture medium at 37° C. and the microplate can be placed back in a cell culture incubator, ready for its experimental use.

The invention comprises to freeze cells directly into HTS microplates, avoiding this way the time consuming steps of cell thawing, cell seeding, cell expanding in flasks, cell lifting, and cell seeding again in a new microplate. The main advantage of the freezing method of the invention is the considerable saving of procedure time. After traditional test procedures of the art, cells must be thawed, grown in flasks until having an appropriate cell number, seeded in 96 well plates, then wait for 24 hours incubation ready for the assay, which will still take between 4 and 5 days. With the method of the invention, cells are directly thawed in the 96 well-plates only needing an overnight post-thawing period. In light of these time advantage, the embodiment of the multi-layer cell freezing/thawing method on 96-well plates is a fast, cheap, robust and feasible method for studying cytotoxicity or for any other cell-based assay.

Apart from the time saving, the present invention avoids potential contamination of the cultures because of the direct use of the cells and the minimization of liquid handling. The use of the freezing method of the invention is not based on the addition of any new reagent, so no new unknown agent effects on the cells are expected. The invention also allows standardization since microplates may be produced in batches, each batch comprising several identical frozen microplates. In addition, a practical solution is provided to assays requiring either the use of adherent cells at various confluence stages or cells synchronized at different cell cycle stages. The method of the invention also provides with a commercial advantage since several cell types may be multiplexed in the same microplate, saving costs associated to purchasing the different individual cell types needed for one single assay. This multiplexing ability is functionally attractive for a wide range of experimental approaches as well as for contributing to a considerable reduction of the budget.

As per the results disclosed herewith, the multi-layer freezing method of the invention is valid in 96 well-plates for HT29 human tumour cells and NIH3T3 fibroblast cells. The viability of the thawed cells in the examples was considerably higher than freezing and thawing the cells following the standard vial method of the art.

The most preferred embodiment of the invention is a HTS format ready-to-use multi-well plate containing al least one triple-layer cell frozen body, said triple-layer frozen body obtained by a method comprising the steps of: freezing a layer of complete culture medium supplemented with at least one antibiotic and serum in said well; adding onto said frozen diluent a layer of cells in form of a solution, the medium of said solution comprising DMSO in suitable concentration; freezing the result of the previous step to obtain a double-layer frozen body; adding, onto said frozen cells on top of the double-layer frozen body, a layer of anoxic complete culture medium and freezing the result to obtain said triple-layer frozen body.

BRIEF DESCRIPTION OF THE FIGURES

A: A first layer of complete cell culture medium is dispensed in each well of a 96 well plate. The plate is then frozen at −70° C. or less.

B: A second layer of cells or cell-like materials containing a cryoprotective agent at 4° C. or less is added on top of the complete culture medium frozen layer. The plate is then frozen at −70° C. or less.

C: Mixture of the two layers as a result of thawing the microplate at 37° C. Dots represent cells suspended in the diluted cryoprotective agent.

D: Adherent cells fall by gravity and are evenly attached on the bottom of the wells after a brief incubation time at 37° C.

DETAILED DESCRIPTION OF PARTICULAR EMBODIMENTS

The following examples are provided in order to demonstrate and further illustrate certain preferred embodiments and aspects of the present invention, however not to be construed as limiting the scope thereof.

EXAMPLE 1

Two-Layer Cell Freezing/Thawing Method on HT29 Colon Carcinoma Cells

HT29 Cells (ATCC, LGC Standards) cultured in endotoxin-free McCoy's 5A complete culture medium supplemented with 10% FCS (Gibco), 100 μg/ml penicillin and 100 IU/ml streptomycin (Sigma-Aldrich) were grown in flasks until they were 80% confluent, and than harvested. Harvesting took place by incubating cells with 5 ml of PBS containing 0.05% EDTA for 2 min, and final detachment was achieved by incubation in 5 ml of PBS with 0.1% trypsin and 0.05% EDTA for another 5 min. Cells were centrifuged at 400×G for 5 min. Then, a total of 4.8 ml of a solution at 4° C. containing 80,000 HT29 cells/50 μl of freezing 80% Mc Coy's, 10% FCS, 10% DMSO (AppliChem) medium was prepared (cell density determined by haemocytometer), forming the no called freezing solution. Besides, 100 μl of complete culture medium was disposed in each cell of a 96-well plate and frozen down to −80° C. Once frozen, the plate is recovered and 50 μl/well of the said freezing solution were added on top each well containing 100 μl of complete culture medium already frozen. The plate was maintained 10 min in a dry ice atmosphere and next moved to a −80° C. freezer for 5 days. As a negative control, another solution of 80,000 HT29 cells/50 μl was frozen in a cryovial along with the 96-well plate and then also moved to a −80° C. freezer to be used as the Vial Control.

Five days later, the frozen 96-well plate was moved to a $CO_2$ incubator at 37° C. At the same time the Vial Control was thawed rapidly in a clean water bath at 37° C. with gentle shaking. 50 μl/well of the Vial Control were seeded on another 96-well plate containing 100 μl/well of warm complete culture medium. One hour after thawing, the medium from all plates was changed by fresh pre-warmed complete culture medium. An MTT assay (Sigma-Aldrich) was performed to all the cells after 24 hours of incubation. The MTT assay is a laboratory test and standard colorimetric assay for measuring the activity of enzymes that reduce MTT to formazan, giving a purple colour. Yellow MTT (3-(4,5-Dimethylthiazol-2-yl)-2,5-diphenyltetrazolium bromide, a tetrazole) is reduced to purple formazan in living cells. An MTT solution stock with 5 mg/ml of PBS 1× was prepared. 100 μl/well of MTT work solution (1:100 in culture medium) were added to the previously thawed cells, and incubated in the $CO_2$ incubator. After 3 hours, the MTT was removed from the plate vvells by aspiration and 200 μl/well of DMSO were added to turn the insoluble purple formazan product into a coloured solution. The absorbance of this solution was quantified in a spectrophotometer (Multiskan Ascent, Thermo Labsystems) at 540 nm.

Figure 1:
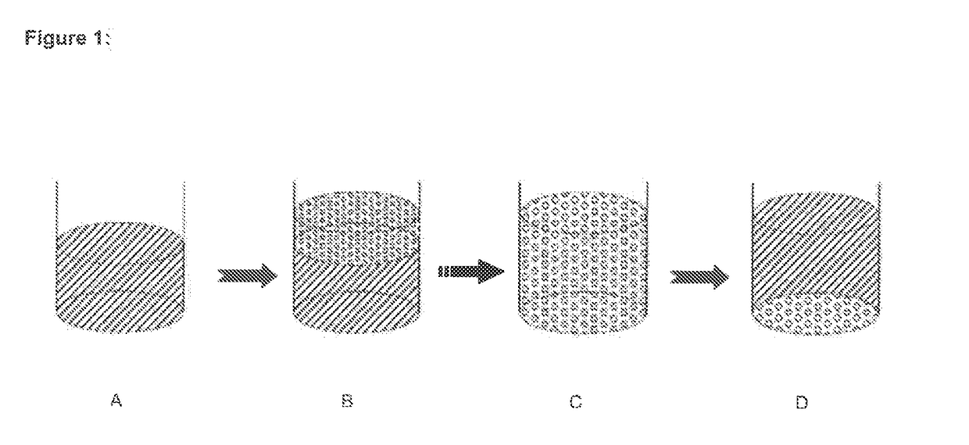
FIG. 1.—Two-step freezing process in one well of a 96-well plate (pictures A & B) followed by thawing (pictures C & D), rendering an auto-cell seeding mechanism once the plate is thawed in a regular cell incubator.
Figure 2:
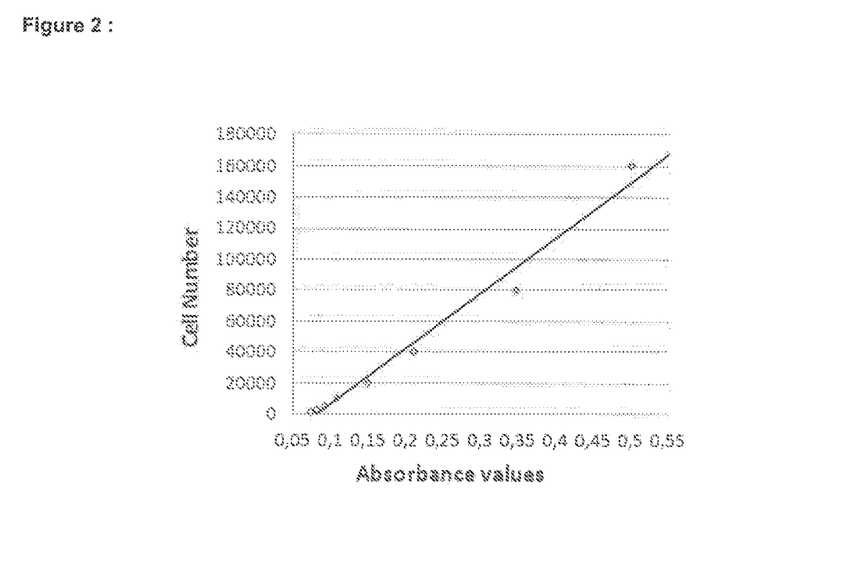
FIG. 2: HT29 Standard Curve. f(x)=357415x−30210; $R^2$=0.98.
Figure 3:
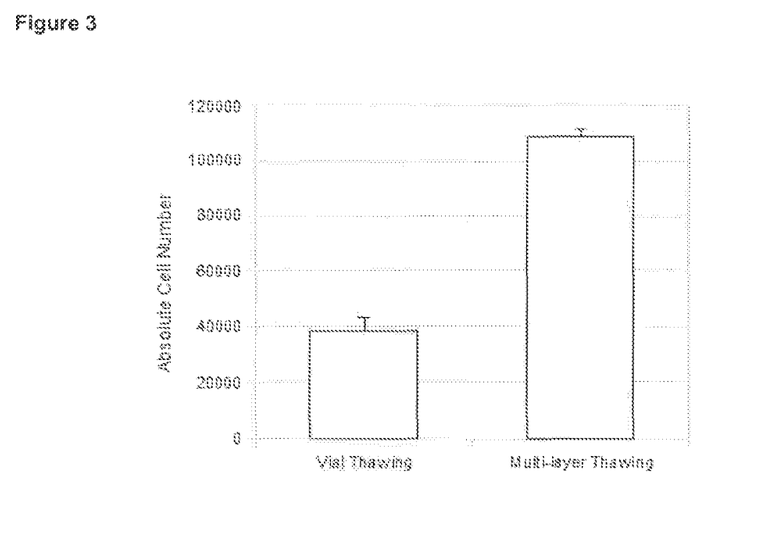
FIG. 3.—Cell Viability in HT29 Cells. It shows a clear increment in cell number viability of the multi-layer freezing/thawing method versus the cells from the Control Vial. Cell number below and above 80,000 cells/well accounts respectively for cell mortality and cell proliferation after 24 hours incubation.

A reference standard curve was created (FIG. 2). HT29 Cells were first incubated in 0.05% EDTA for 2 min. Final detachment was achieved by incubation in 0.1% typsin and 0.05% EDTA for another 5 min. Cells were centrifuged at 400×G for 5 min. Cell density was determined by counting the cells using a haemocytometer. The dilution series were generated in the wells of a 96-well plate. Cell number ranged from 1250 to 160000 cells in volumes of 200 μl. As soon as the cells were properly attached, the MTT assay was performed as related above.

EXAMPLE 2

Two-Layer Cell Freezing/Thawing Method on NIH3T3 Murine Fibroblasts

NIH3T3 cells (ATCC, LGC Standards) cultured in endotoxi-free DMEM medium (Sigma-Aldrich) supplemented with 10% FCS, 100 μg/ml penicillin and 100 IU/ml streptomycin (Sigma-Aldrich) were grown in flasks until they were 80% confluent, and then harvested. Harvesting took place by incubating cells in 5 ml of PBS with 0.05% EDTA for 2 minutes, and final detachment was achieved by incubation in 0.1% trypsin and 0.05% EDTA for another 5 minutes. Cells were centrifuged at 400×G for 5 minutes. Then a total of 4.8 ml of a solution at 4° C. containing 80,000 NIH3T3 cells/50 μl of freezing 80% DMEM, 10% FCS, 10% DMSO (AppliChem) medium was prepared (cell density determined by haernocytometer), forming the so-called freezing solution. Besides, 100 μl of complete culture medium was disposed in each cell of a 96-well plate and frozen down to −80° C. Once frozen, the plate is recovered and 50 μl/well of the said freezing solution were added on top each well containing 100 μl of complete culture medium already frozen. The plate was maintained 10 min in a dry ice atmosphere and next moved to a −80° C. freezer for 5 days. As a negative control, another solution of 80,000 HT29 cells/50 μl was frozen in a cryovial along with the 96-well plate and then also moved to a −80° C. freezer to be used as the Vial Control.

Five days later, the frozen 96-well plate was moved to a CO$_2$ incubator at 37° C. At the same time the Vial Control was thawed rapidly in a clean water bath at 37° C. with gentle shaking, 50 µl/well of the Vial Control were seeded on another 96-well plate containing 100 µl/well of warm complete culture medium. One hour after thawing, the medium from all plates was changed by fresh pre-warmed complete culture medium. An MTT assay (Sigma-Aldrich) was performed to all the cells after 24 hours of incubation. An MTT solution stock with 5 mg/ml of PBS 1× was prepared. 100 µl/well of MTT work solution (1:100 in culture medium) were added to the previously thawed cells, and incubated in the CO$_2$ incubator. After 3 hours, the MTT was removed from the plate wells by aspiration and 200 µl/well of DMSO were added to turn the insoluble purple formazan product into a coloured solution. The absorbance of this solution was quantified in a spectrophotometer (Multiskan Ascent, Thermo Labsystems) at 540 nm.

Figure 4:
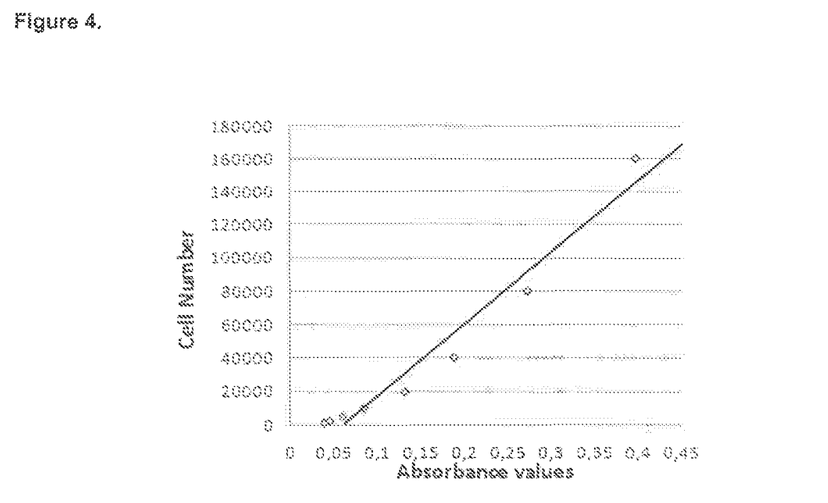
FIG. 4.—NIH3T3 Standard Curve. f(x)=422129x−24554. R2=0.96
Figure 5:
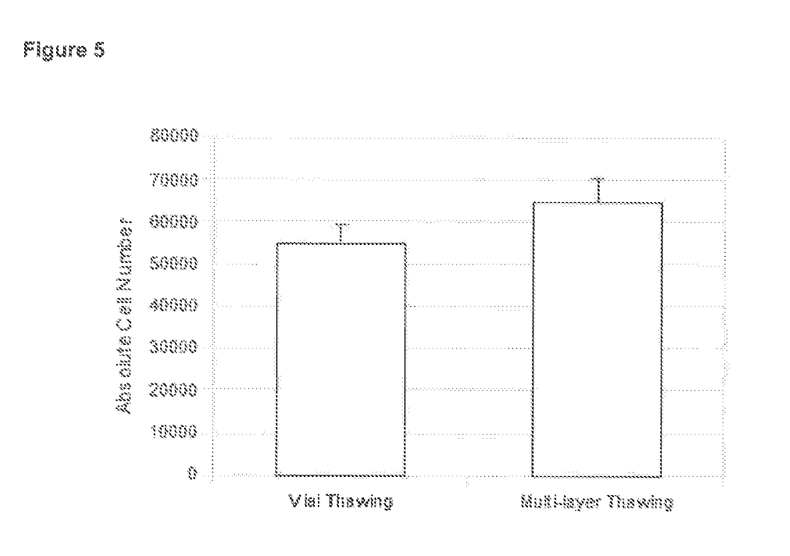
FIG. 5.—Cell Viability in NIH3T3 Cells. It shows a slight increment in cell number viability after 24 hours incubation when comparing the multi-layer freezing/thawing method versus the cells of the Control Vial.
Figure 6:
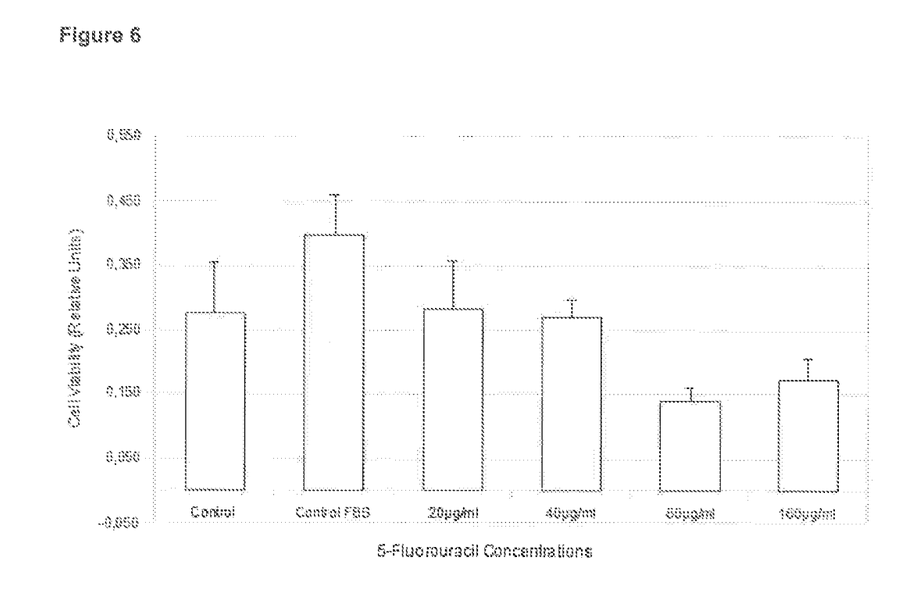
FIG. 6.—Concentration dependent cytotoxic response of BALB3T3 cells upon 5-Fluoracil treatments.
Figure 7:
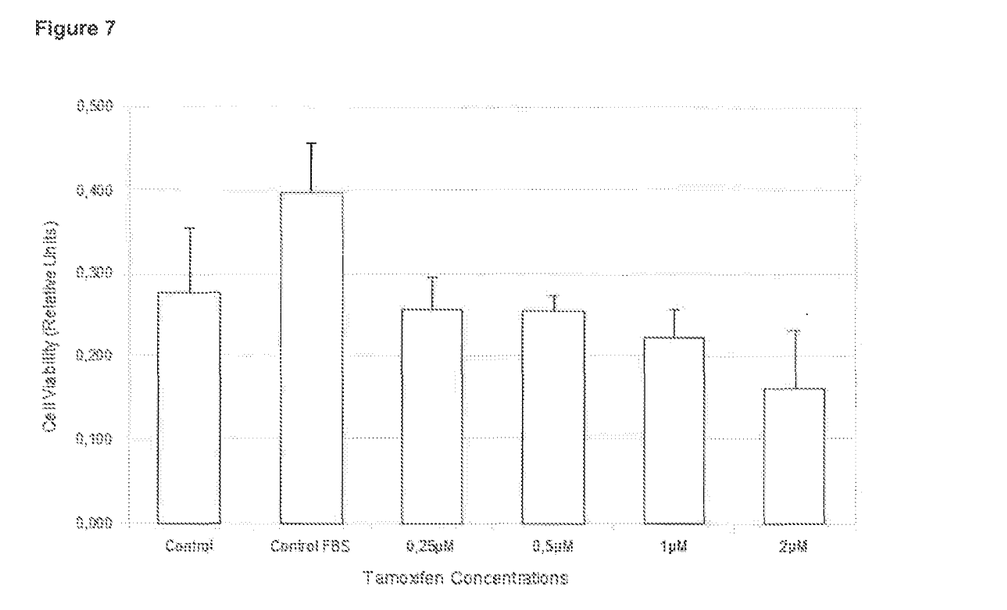
FIG. 7.—Concentration dependent cytotoxic response of BALB3T3 cells upon Tamoxifen treatments.
Figure 8:
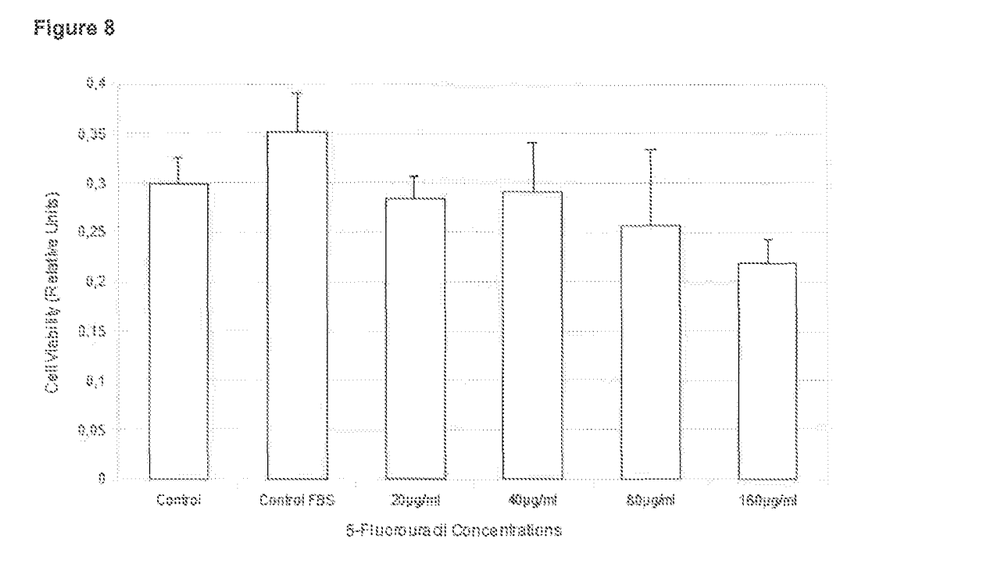
FIG. 8.—Concentration dependent cytotoxic response of Smac cells upon 5-Fluorouracil treatments.
Figure 9:
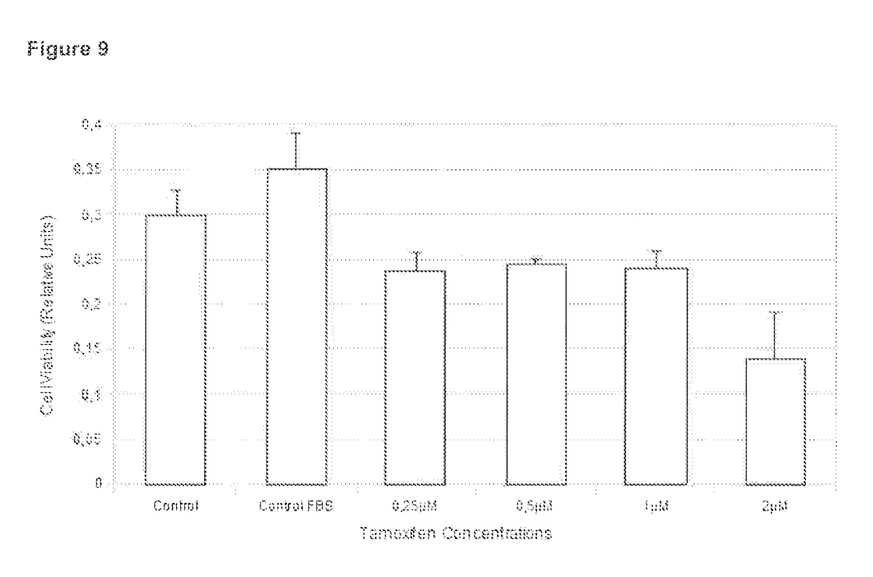
FIG. 9.—Concentration dependent cytotoxic response of Smac cells upon Tamoxifen treatments.

A reference standard curve was created (FIG. 4). NIH3T3 cells were first incubated in 0.05% EDTA for 2 min. Final detachment was achieved by incubation in 0.1% trypsin and 0.05% EDTA for another 5 min. Cells were centrifuged at 400×G for 5 min. Cell density was determined by counting the cells using a haemocytometer. The dilution series were generated in the wells of a 96-well plate. Cell number ranged from 1,250 to 160,000 cells in volumes of 200 µl. As soon as the cells were properly attached, the MTT assay was performed as related above.

EXAMPLE 3

Cytotoxic Test

Balb3T3 (ATCC, LCC Standards) fibroblasts and smooth muscle aortic cells (SMAC, freshly isolated from Sprague Dawley rats, Harlan Laboratories) primary cells were cultured in complete culture medium consisting of endotoxin-free DMEM (Sigma-Aldrich) supplemented with 10% FCS, 100 µg/ml penicillin and 100 IU/ml streptomycin (Sigma-Aldrich). SMAC cells were isolated from a single male rat aorta: the aorta was carefully dissected from its origin at the left ventricle to the iliac bifurcation and cells were isolated by enzymatic digestion of the tissue with collagenase type II (Worthington). The resulting cells were allowed to grow for twelve days prior to cryopresentation. Both cell types were grown in flasks until they were 80% confluent and then harvested. Harvesting took place by incubating cells in 5 ml of PBS with 0.05% EDTA for 2 minutes, and final detachment was achieved by incubation in 0.1% trypsin and 0.05% EDTA for another 5 minutes. Cells were centrifuged at 400×G for 5 minutes. Then, a total of 4.8 ml of a solution at 4° C. containing 50,000 cells/50 µl of freezing 80% DMEM, 10% FCS, 10% DMSO (AppliChem) medium was prepared (cell density determined by haemocytometer), forming the so-called freezing solution. Besides, 100 µl of complete culture medium was disposed in each cell of a 96-well plate and frozen down to −80° C. Once frozen, the plate is recovered and 50 µl/well of the said freezing solution were added on top each well containing 100 µl of complete culture medium already frozen. The plate was maintained 10 min in a dry ice atmosphere and next moved to a −80° C. freezer for 5 days. Five days later, the frozen 96-well plate was moved to a CO$_2$ incubator at 37° C. One hour after thawing, the medium from all plates was changed by fresh pre-warmed complete culture medium, Twenty four hours post-thawing, both cell types Balb3T3 and SMAC cells, were incubated with 20, 40, 80 and 100 µg/ml of 5-Fluorouracil and 0.02, 1.25, 2.5 and 5 µM of Tamoxifen respectively. Control cells received basal medium and control-FBS cells received complete medium. Experiments were done in triplicate. Twenty four hours later a MTT assay was performed and cytotoxicity was calculated according to the absorbance values.

An MTT solution stock with 5 mg/ml of PBS 1× was prepared. Then, 100 µl/well of MTT work solution (1:100 in culture medium) were added to the previously thawed plates and was incubated during 3 hours in the CO$_2$ incubator. The MTT was removed from the plate wells and 200 µl/well of DMSO were added to dissolve the insoluble purple formazan product into a coloured solution. The absorbance of this solution was quantified by measuring at 540 nm by a spectrophotometer (Multiskan Ascent, Thermo Labsystems).

The invention claimed is:

1. A method of freezing cells or cell-like materials or non-human embryos, said method comprising the steps of:
    a) freezing a layer of biologically acceptable liquid diluent in a container, to create a frozen diluent layer;
    b) adding on top of said frozen diluent layer, a layer of a solution comprising said cells or cell-like materials or non-human embryos and at least one cryoprotective agent in suitable concentration; and
    c) freezing the result of the previous step to obtain a double-layer frozen body with the frozen diluent layer on the bottom and the frozen cells or cell-like materials or non-human embryos solution and the cryoprotective agent on top.

2. The method according to claim 1, the volume of said cells or cell-like materials or non-human embryos solution layer is equal or less than half the volume of said liquid diluent layer.

3. The method according to claim 1, further comprising the steps of:
    d) adding, onto the frozen cells or cell-like materials or non-human embryos solution on top of the double-layer frozen body, a layer of hypoxic biologically acceptable liquid diluent; and
    e) freezing the result of the previous step to obtain a triple-layer frozen body.

4. The method according to claim 3, wherein said hypoxic biologically acceptable liquid diluent is an anoxic biologically acceptable liquid diluent.

5. The method according to claim 1, wherein said biologically acceptable liquid diluent is a complete cell culture medium.

6. The method according to claim 5, said complete cell culture medium is supplemented with at least one antibiotic and/or serum.

7. The method according to claim 1, wherein said cryogenic agent is selected from the group consisting of DMSO, glycerol, polyvinyl-pyrrolidone, ethylene glycol, methanol, methyl acetamide and sugars.

8. The method according to claim 1, wherein said cells are microorganisms.

9. The method according to claim 1, wherein said cells are plant cells.

10. The method according to claim 1, wherein said cells are animal cells.

11. The method according to claim 10, wherein said animal cells are selected from the group consisting of tumour cell lines, immortalized cell lines, continuous cell lines, genetically modified cell lines, division arrested cells, stem cells, induced pluripotent stem cells and primary isolated cells.

12. The method according to claim 10, wherein said primary isolated cells are selected from the group consisting of epithelial cells, endothelial cells, mesenchymal cells, hematopoietic cells.

13. The method according to claim 10, wherein said animal cells are mammal cells.

14. The method according to claim 10, wherein said animal cells are oocytes or sperm.

15. The method of claim 1, wherein the cryoprotective agent has a molecular weight that is higher than the molecular weight of the diluent.

16. The method of claim 1, wherein the layer of the solution comprising the cryoprotective agent and cells or cell-like material or non-human embryos has a volume that is equal to or less than a volume of the diluent layer.

17. A method of freezing cells or cell-like materials or non-human embryos, said method comprising the steps of:
   a) freezing a layer of biologically acceptable liquid diluent in a container, to create a frozen diluent layer;
   b) adding on top of said frozen diluent layer, a layer of a solution comprising said cells or cell-like materials or non-human embryos and at least one cryoprotective agent in suitable concentration;
   c) freezing the result of the previous step to obtain a double-layer frozen body with the frozen diluent layer on the bottom and the frozen cells or cell-like materials or non-human embryos solution on top; and
   d) thawing the double-layer frozen body, whereby the diluent layer and the solution comprising the cryoprotective agent and cells or cell-like material or non-human embryos mix, taking the concentration of the cryoprotective agent to a non-pathogenic concentration.

18. The method of claim 17, wherein the volume of said cells or cell-like materials or non-human embryos solution layer is equal to or less than half the volume of said liquid diluent layer.

19. The method according to claim 17, further comprising the steps of:
   d) prior to thawing, adding, onto the frozen cells or cell-like materials or non-human embryos solution on top of the double-layer frozen body, a layer of hypoxic biologically acceptable liquid diluent; and
   e) freezing the result of the previous step to obtain a triple-layer frozen body.

20. The method of claim 17, wherein the cryoprotective agent has a molecular weight that is higher than the molecular weight of the diluent.

* * * * *